United States Patent [19]

Krauss

[11] Patent Number: 4,734,527

[45] Date of Patent: Mar. 29, 1988

[54] PROCESS FOR PREPARING 2,6-DI-TERTIARYBUTYL-4-MERCAPTOPHENOL

[75] Inventor: Richard C. Krauss, Midland, Mich.

[73] Assignee: Merrell Dow Pharmaceuticals Inc., Cincinnati, Ohio

[21] Appl. No.: 920,813

[22] Filed: Oct. 17, 1986

[51] Int. Cl.$^4$ ............................................. C07C 149/36
[52] U.S. Cl. ...................................... 568/47; 568/23; 568/62
[58] Field of Search .............................. 568/47, 62, 23

[56] References Cited

U.S. PATENT DOCUMENTS

| | | | |
|---|---|---|---|
| 3,479,407 | 11/1969 | Laufer | 568/47 |
| 3,576,883 | 4/1971 | Neuworth | 568/47 |
| 3,678,115 | 7/1972 | Fujisawa et al. | 568/23 |
| 3,718,699 | 2/1973 | Fujisawa et al. | 568/23 |
| 3,812,192 | 5/1974 | Gabler et al. | 568/23 |
| 3,952,064 | 4/1976 | Whalley | 568/23 |

FOREIGN PATENT DOCUMENTS

| | | |
|---|---|---|
| 1290132 | 9/1972 | United Kingdom . |
| 1348491 | 3/1974 | United Kingdom . |
| 1425278 | 2/1976 | United Kingdom . |
| 1443329 | 7/1976 | United Kingdom . |

OTHER PUBLICATIONS

Translation of Japan Kokai No. 163536/79, published Dec. 26, 1979.
Translation of Japan Kokai No. 17316/80, published Feb. 6, 1980.
Translation of Japan Kokai No. 904/80, published Jan. 22, 1980.
R. Galiano et al, Chem. Abstracts 95:150171g, (1981).
Derwent Abstract of JA 7328425, published Sep. 1, 1973.

*Primary Examiner*—Mary E. Ceperley

[57] ABSTRACT

In a process for making 2,6-di-tertiarybutyl-4-mercaptophenol by the Zn/acid reduction of bis (3,5-di-tertiarybutyl-4-hydroxyphenyl)polysulfide the addition of catalytic amounts of lead to the zinc reagent results in substantial improvement in the process.

18 Claims, No Drawings

PROCESS FOR PREPARING 2,6-DI-TERTIARYBUTYL-4-MERCAPTOPHENOL

BACKGROUND OF INVENTION

1. Field of the Invention

This invention relates to a novel improvement in the process of preparing 2,6-di-tertiarybutyl-4-mercaptophenol by a zinc-acid reduction of bis(3,5-di-tertiarybutyl-4-hydroxyphenyl)polysulfide in the presence of a catalytic amount of lead. The addition of catalytic amounts of lead to the zinc reagent increases the reduction efficiency of the above reaction. The above process represents an intermediate step for making 4,4'-isopropylidenedithio-bis-(2,6-di-tertiarybutylphenol), which has been described in U.S. Pat. No. 3,576,883 as an effective pharmaceutical agent for the reduction of serum cholesterol and has been approved for marketing in the United States by the Food and Drug Administration (FDA).

2. Description of Prior Art

The reduction of bis(3,5-di-tertiarybutyl-4-hydroxyphenyl)polysulfide in the presence of zinc/HCl is disclosed in U.S. Pat. Nos. 3,952,064 and 3,479,407 and in Japanese patent application No. 73-28425. No mention, however, is made of the utility of a catalytic amount of lead in this reaction. U.S. Pat. No. 3,479,407 discloses the preparation of bis(3,5-di-tertiarybutyl-4-hydroxyphenyl)polysulfide by sulfurization of 2,6-di-tertiarybutylphenol with sulfur monochloride in the presence of an iodine catalyst. The Polysulfide can then be reduced to the corresponding mercaptophenol, i.e., 2,6-di-tertiarybutyl-4-mercaptophenol, which can be condensed using acetone under acidic conditions to form 4,4'-iso-propylidenedithio-bis-(2,6-di-tertiarybutylphenol), as described in U.S. Pat. No. 3,576,883. This reaction sequence is as follows:

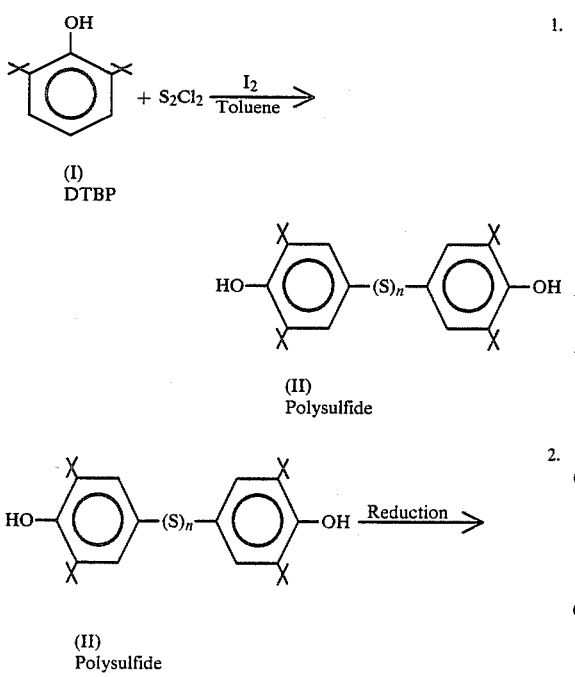

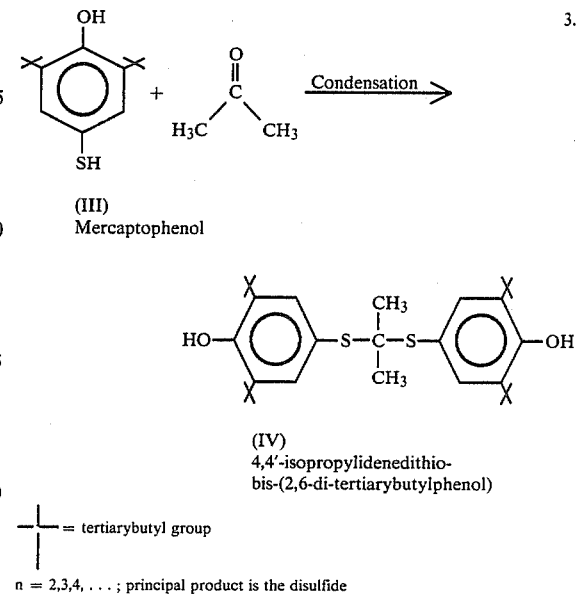

$-\underset{|}{\overset{|}{\text{L}}}-$ = tertiarybutyl group n = 2,3,4, ... ; principal product is the disulfide The Zn/HCl reduction of the Polysulfide (II) to the corresponding Mercaptophenol (III) is inconsistent, resulting in variable, incomplete reductions which require multiple cycles through the reductive step to obtain satisfactory yields. The present invention which comprises an improvement in this process results in consistent high-yield reductions of the Polysulfide (II) to the corresponding Mercaptophenol (III) and substantially improves the process of making 4,4'-iso-propylidenedithio-bis-(2,6-di-tertiarybutylphenol).

SUMMARY OF THE INVENTION

The following terms are used herein as follows:
"DTBP" refers to as 2,6-di-tertiarybutylphenol (I).
"Polysulfide" and "Bis(3,5-di-tertiarybutyl-4-hydroxyphenyl)polysulfide" both are used to refer to one or more species of bis(3,5-di-tertiarybutyl-4-hydroxyphenyl)polysulfide (II) including the di-, tri-, tetra-, and other higher order sulfides, and including single species as well as mixtures thereof. Typically, the Polysulfide is a mixure of two or more species with the disulfide present in amounts greater than other species.
"Mercaptophenol" refers to 2,6-di-tertiarybutyl-4-mercaptophenol (III).

The novel improvement in the process of the Zn/acid reduction of Polysulfide (II) to Mercaptophenol (III) comprises the addition of a catalytic amount of lead to the zinc reagent in order to provide a consistent high-yield reduction.

In general, zinc reagent is contacted with a catalytic amount of lead, i.e., an amount which is sufficient to provide a substantial increase in yield of Mercaptophenol (III) or a substantial decrease in the reaction time required for the reduction of Polysulfide (II) in comparison to that obtained with zinc reagent in the absence of that amount of added lead. Preferably, an aqueous slurry of zinc dust is agitated with sufficient PbCl$_2$, or other soluble lead salt such as lead acetate, to provide from about 1200 to about 5000 parts by weight of lead per million parts by weight of zinc and more preferably to provide from about 2700 to about 3300 parts by weight of lead per million parts by weight of zinc. This aqueous slurry of zinc dust and soluble lead salt is preferably agitated at ambient temperature for about 0.5 to about 1.0 hour in the presence of Polysulfide (II). The reduction of Polysulfide (II) to Mercaptophenol (III) is initiated with the addition of acid, preferably HCl, to this mixture. Other solvents, such as acetic acid, which are capable of supporting lead and zinc ion and are compatible with an acid-mediated reduction of the Polysulfide (II) can also be used. Although the above order of mixing the reactants is preferred, i.e., the addition of acid last to initiate the reaction, it is understood that other orders of addition of the reactants are encompassed by the present invention. In addition, zinc can be pre-treated with appropriate amounts of lead and stored for future use.

It is likely that the contacting of the zinc catalyst with lead ion results in the reduction of the lead ion to elemental lead and the consequent deposition of lead on the surface of the zinc. This is described by the following reaction scheme:

$$Pb^{+2} + Zn° \rightarrow Pb° + Zn^{+2}$$

The mechanism for the Zn/acid reduction of the Polysulfide (II) to Mercaptophenol (III) in the presence of a catalytic amount of lead is thought to involve the following sequence in which lead cleaves the disulfide bond of the Polysulfide (II) in an initial step followed by an electrochemical reduction of the lead mercaptide salt to give the Mercaptophenol (III).

$$R—S—S—R + Pb° \rightarrow Pb(SR)_2 \quad (II)$$

$$Pb(SR)_2 + 2H^+ + Zn° \rightarrow 2RSH + Pb° + Zn^{+2} \quad (III)$$

The present invention, however, is understood not to be limited by any particular theory of mechanism in bringing about the improvement in the process of preparing the Mercaptophenol (III).

The following examples illustrate that the addition of lead to zinc catalyst in amounts sufficient to provide a final concentration of about 1100 ppm to about 7000 ppm of lead, results in substantial improvement in product yield in the Zn/acid reduction of Polysulfide (II) to Mercaptophenol (III).

EXAMPLE 1

In a series of runs, a Zn/HCl reduction of Polysulfide (II) to Mercaptophenol (III) was carried out with a zinc reagent in the presence and absence of various amounts of added lead.

A 250 milliliter (ml) flask was charged with 12.2 grams (0.187 moles) of zinc (which had been analyzed and found to contain about 140 parts per million of lead) and 100 ml of sulfurization mixture which contained Polysulfide (II) formed by reacting 0.25 moles of DTBP (I) with sulfur monochloride in the presence of an iodine catalyst. 32 ml of water and 32 ml of 37% HCl were added and the reaction mixture was heated over about 10 minutes to about 70° C. and held. The reductions were run until no more product was being formed, generally 200 to 250 minutes.

This reaction was repeated with the addition of lead to the zinc reagent as follows: A 250 ml flask was charged with 12.2 grams (0.187 moles) of the same zinc as above (containing about 140 ppm of lead), 100 ml of sulfurization mixture from 0.25 moles of DTBP, and 32 ml of a PbCl$_2$ solution in water. The amount of PbCl$_2$ was varied in different runs to provide a final lead concentration of from about 1100 to about 6200 parts of lead per million parts of zinc. The mixture was agitated for 1 hour at 25° C. before adding 32 ml of 37% HCl and heating as described above.

As shown in Table 1, the reduction results in a 33% yield in the absence of added lead, whereas the addition of lead to the zinc reagent to provide a total of 1100 to 6200 ppm of lead results in a 79 to 88% yield. These results demonstrate that the addition of catalytic amounts of lead to the zinc reagent provides a substantial increase in the yield of the reduction product over that found with the zinc reagent in the absence of added lead.

TABLE 1

| | Results of Zn/HCl Reduction With and Without the Addition of Lead | |
|---|---|---|
| Run | Added Pb (ppm) | % Yield |
| 1 (Control) | 0 | 33 |
| 2 | 1100 | 79 |
| 3 | 2900 | 87 |
| 4 | 6200 | 88 |

EXAMPLE 2

In another experiment, the time course of the reduction was followed using a zinc reagent in the presence and absence of added lead.

A 1-liter flask was charged with 83 grams (1.27 moles) of zinc (which was analyzed and found to contain about 200 ppm of lead), 100 ml of water, and 407 grams of water-washed sulfurization mixture containing Polysulfide (II). The slurry was warmed to 78° C. and 332 grams of 37% hydrochloric acid was added over the course of about 30 minutes while maintaining constant stirring. The disappearance of the Polysulfide (II) during the reaction was monitored by measuring the peak area of the disulfide as analyzed by HPLC (High Pressure Liquid Chromotography) in samples of the reaction mixture taken at various times during the reaction.

This reaction was then repeated with the addition of lead to the zinc reagent as follows: A 1-liter flask was charged with 83 grams (1.27 moles) of the same zinc as above (containing about 200 ppm of lead), 100 ml of water, 0.196 grams (0.704 mmoles) of PbCl$_2$, and 407 grams of water-washed sulfurization mixture containing Polysulfide (II). The resulting slurry was agitated at ambient temperature for about 30 minutes before addition of 332 grams of 37% HCl and monitored as described above. This zinc reagent was treated with a quantity of PbCl$_2$ calculated to provide a final lead concentration of about 2000 parts by weight of lead per million parts by weight of zinc.

As shown in Table 2, the zinc to which no lead had been added (about 200 ppm of lead) provided a 7% decrease in the Polysulfide (II) after 115 minutes of reaction time (Run 1), whereas the zinc to which lead had been added (about 2000 ppm of lead) provided a 74% decrease by 90 minutes and essentially complete disappearance of Polysulfide (II) by 150 minutes (Run 2). These results demonstrate that the addition of lead to a zinc reagent provides a substantial improvement in the reaction time required for reduction of Polysulfide (II) to the Mercaptophenol (III) product.

TABLE 2

Time Course of Zn/HCl Reduction With and Without the Addition of Lead

| Reaction Time Minute | % Decrease in Polysulfide (II)* | |
| --- | --- | --- |
| | Run 1 (No Added Pb) | Run 2 (Added Pb) |
| 0 | 0.0 | 0.0 |
| 13 | 3.0 | 0.0 |
| 26 | 3.1 | 9.0 |
| 43 | — | 28.0 |
| 44 | 6.0 | — |
| 90 | — | 74.0 |
| 115 | 7.0 | — |
| 150 | — | 97.0 |

*The decrease in Polysulfide (II) is measured as a % decrease in HPLC peak area of the disulfide peak per mg of reaction mixture. The disulfide is the most abundant and difficult of the Polysulfides (II) to reduce; its peak area as a function of reaction time is a measure of the degree and efficiency of this reduction.

It is understood that athe foregoing detailed description is given merely by way of illustration and that many modifications may be made therein without departing from the spirit or scope of the present invention.

I claim:

1. In a process for making 2,6-ditertiarybutyl-4-mercaptophenol by reduction of a bis(3,5-ditertiarybutyl-4-hydroxyphenyl)polysulfide in the presence of a zinc catalyst and acid, the improvement which comprises contacting the zinc with an amount of lead which is catalytic for said reduction prior to carrying out the reduction.

2. Process of claim 1 wherein the reaction mixture contains from about 1200 to about 5000 parts by weight of lead per million parts by weight of zinc.

3. Process of claim 1 wherein the reaction mixture contains from about 2700 to about 3300 parats by weight of lead per million parts by weight of zinc.

4. In a process of making 2,6-ditertiarybutyl-4-mercaptophenol by sulfurization of 2,6-ditertiarybutylphenol and reduction of the sulfurization product in the presence of a zinc catalyst and acid, the improvement which comprises contacting the zinc with an amount of lead which is catalytic for said reduction prior to carrying out the reduction.

5. Process of claim 4 wherein the reaction mixture contains from about 1200 to about 5000 parts by weight of lead per million parts by weight of zinc.

6. Process of claim 4 wherein the reaction mixture contains from about 2700 to about 3300 parts by weight of lead per million parts by weight of zinc.

7. In a process for making 4,4'-isopropylidene-dithio-bis-(2,6-di-tertiarybutylphenol) by reduction of a bis(3,5-di-tertiarybutyl-4-hydroxyphenyl)polysulfide in the presence of a zinc catalyst and acid, and reacting the reduction product with acetone under acidic conditions, the improvement which comprises contacting the zinc with an amount of lead which is catalytic for said reduction prior to carrying out the reduction.

8. Process of claim 7 wherein the reaction mixture contains from about 1200 to about 5000 parts by weight of lead per million parts by weight of total zinc.

9. Process of claim 7 wherein the reaction mixture contains from about 2700 to about 3300 parts by weight of lead per million parts by weight of zinc.

10. In a process for making 2,6-di-tertiarybutyl-4-mercaptophenol by reduction of a bis(3,5-di-tertiarybutyl-4-hydroxyphenyl)polysulfide in the presence of a zinc catalyst and acid, the improvement which comprises conducting the reduction in the presence of an amount of lead which is catalytic for said reduction.

11. Process of claim 10 wherein the reaction mixture contains from about 1200 to about 5000 parts by weight of lead per million parts by weight of zinc.

12. Process of claim 10 wherein the reaction mixture contains from about 2700 to about 3300 parts by weight of lead per million parts by weight of zinc.

13. In a process for making 2,6-di-tertiarybutyl-4-mercaptophenol by sulfurization of 2,6-di-tertiarybutylphenol and reduction of the sulfurization product in the presence of a zinc catalyst and acid, the improvement which comprises conducting said reduction in the presence of an amount of lead which is catalystic for said reduction.

14. Process of the reduction step of claim 13 wherein the reaction mixture contains from about 1200 to about 5000 parts by weight of lead per million parts by weight of zinc.

15. Process of the reduction step of claim 13 wherein the reaction mixture contains from about 2700 to about 3300 parts by weight of lead per million parts by weight of zinc.

16. In a process for making 4,4'-isopropylidenedithio-bis-(2,6-di-tertiarybutylphenol) by reduction of a bis(3,5-di-tertiarybutyl-4-hydroxyphenol)polysulfide in the presence of a zinc catalyst and acid, and reacting the reduction product with acetone under acidic conditions, the improvement which comprises conducting said reduction in the presence of an amount of lead which is catalytic for said reduction.

17. Process of claim 16 wherein the reaction mixture contains from about 1200 to about 5000 parts by weight of lead per million parts by weight of zinc.

18. Process of claim 16 wherein the reaction mixture contains from about 2700 to about 3300 parts by weight of lead per million parts by weight of zinc.

* * * * *